US00PP32372P2

(12) United States Plant Patent
Hazama

(10) Patent No.: US PP32,372 P2
(45) Date of Patent: Oct. 20, 2020

(54) ***DIEFFENBACHIA* PLANT NAMED 'COOL BEAUTY'**

(50) Latin Name: *Dieffenbachia sanguine schott*
Varietal Denomination: COOL BEAUTY

(71) Applicant: Kaneya Co., LTD, Chita-Gun (JP)

(72) Inventor: Takuya Hazama, Kukuoka (JP)

(73) Assignee: Kaneya Co., Ltd. (JP)

( * ) Notice: Subject to any disclaimer, the term of this patent is extended or adjusted under 35 U.S.C. 154(b) by 7 days.

(21) Appl. No.: 16/602,570

(22) Filed: Oct. 31, 2019

(51) Int. Cl.
*A01H 5/02* (2018.01)

(52) U.S. Cl.
USPC ..... Plt./378

(58) Field of Classification Search
USPC ..... Plt./378
CPC ..... A01H 5/02
See application file for complete search history.

(56) References Cited

PUBLICATIONS

PLUTO Plant Variety Database Apr. 29, 2020.*

* cited by examiner

*Primary Examiner* — Annette H Para
(74) *Attorney, Agent, or Firm* — Cassandra Bright

(57) ABSTRACT

A new and distinct *Dieffenbachia* cultivar named 'COOL BEAUTY' is disclosed, characterized marginal white colored foliage followed by a green interior halo and lighter green and yellow-green innermost section. Variegation occurs on upper and lower leaf surfaces. Plants produce abundant short foliage. The new variety is a *Dieffenbachia*, normally produced as an indoor ornamental container plant.

2 Drawing Sheets

Latin name of the genus and species: *Dieffenbachia sanguine* schott.

Variety denomination: 'COOL BEAUTY'.

BACKGROUND OF THE INVENTION

The new *Dieffenbachia* cultivar is a product of chance discovery by the inventor at a commercial greenhouse in Japan.

The parent is the unpatented variety *Dieffenbachia sanguine* schott 'Camille'. The new variety was discovered as a naturally occurring whole plant mutation among a population of tissue culture propagated plants used for commercial production of the parent variety.

First asexual reproduction of the new cultivar 'COOL BEAUTY' was performed by tissue culture at a commercial laboratory in Japan during 2015. Multiple generations have been produced, and have shown that the unique features of this cultivar are stable and reproduced true to type in successive generations.

SUMMARY OF THE INVENTION

The cultivar 'COOL BEAUTY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COOL BEAUTY' These characteristics in combination distinguish 'COOL BEAUTY' as a new and distinct *Dieffenbachia* cultivar:

1. Distinct white foliage margin.
2. Short foliage.
3. Abundant leaf production.
4. Distinct variegated foliage on both upper and lower surfaces.

PARENT COMPARISON

Plants of the new cultivar 'COOL BEAUTY' are comparable to the parent *Dieffenbachia* 'Camille', unpatented. The two *Dieffenbachia* varieties are similar in most horticultural characteristics however, the new variety 'COOL BEAUTY' differs in the following:

1. Parent has marginal green colored foliage with white and yellow color in center of leaves, new variety has marginal white colored foliage followed by a green interior halo and lighter green and yellow-green innermost section.
2. Leaf venation of the new variety is green, the parent variety has a white/yellow colored venation.
3. Leaf length on new variety is shorter than parent variety.

COMMERCIAL COMPARISON

Plants of the new cultivar 'COOL BEAUTY' are comparable to the variety *Dieffenbachia* 'Tropic Marianne'. The two *Dieffenbachia* varieties are similar in most horticultural characteristics however, the new variety 'COOL BEAUTY' differs in the following:

1. The new variety has marginal white colored foliage followed by a green interior halo and lighter green and yellow-green innermost section. This comparator has yellow foliage with a thick green margin.

2. Leaves of the new variety are smaller than foliage of this comparator.

BRIEF DESCRIPTION OF THE PHOTOGRAPHS

DETAILED BOTANICAL DESCRIPTION

Figure 1:
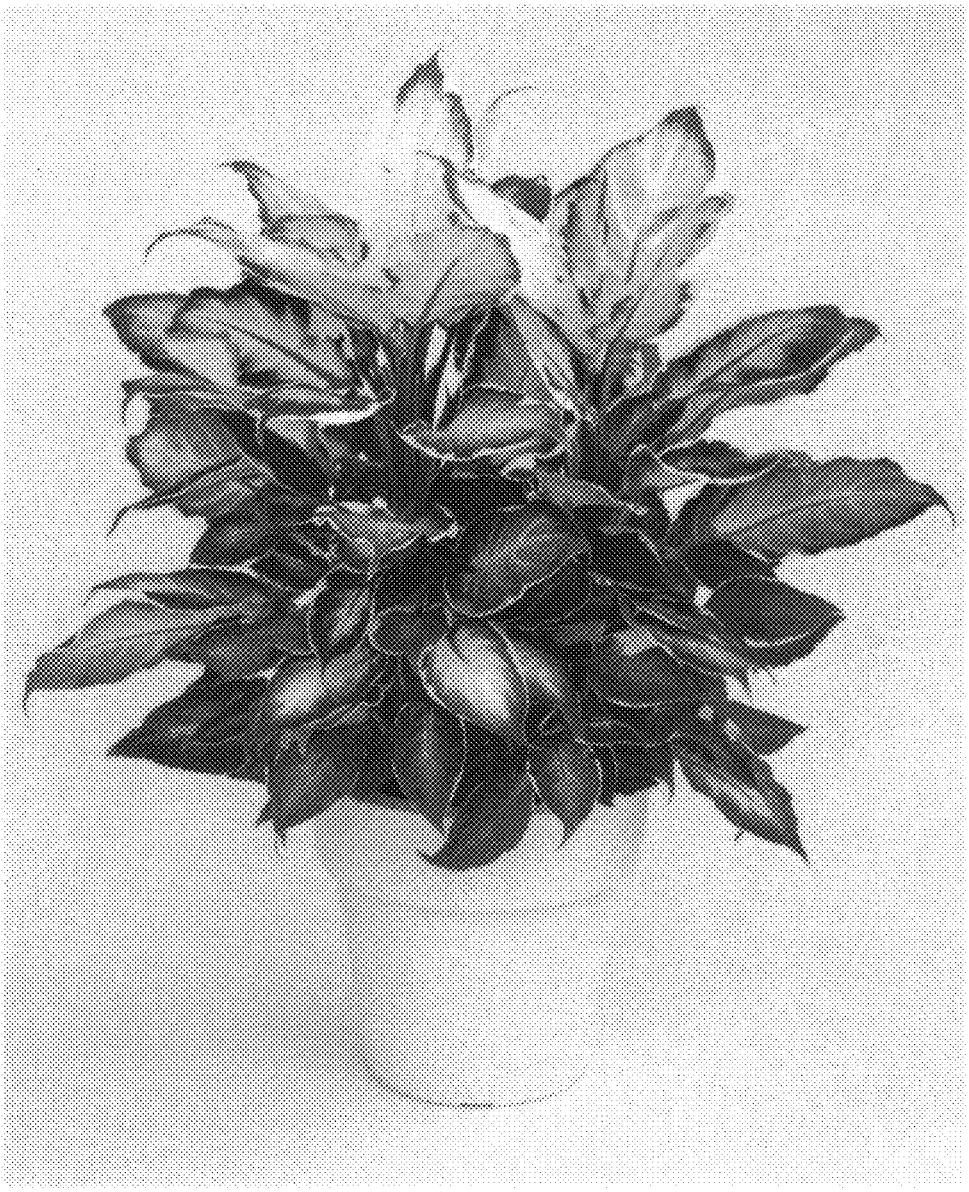
FIG. 1 illustrates in full color a plant of 'Cool Beauty' in a 16 cm pot, approximately 12 months old from a single rooted tissue culture plantlet.
Figure 2:
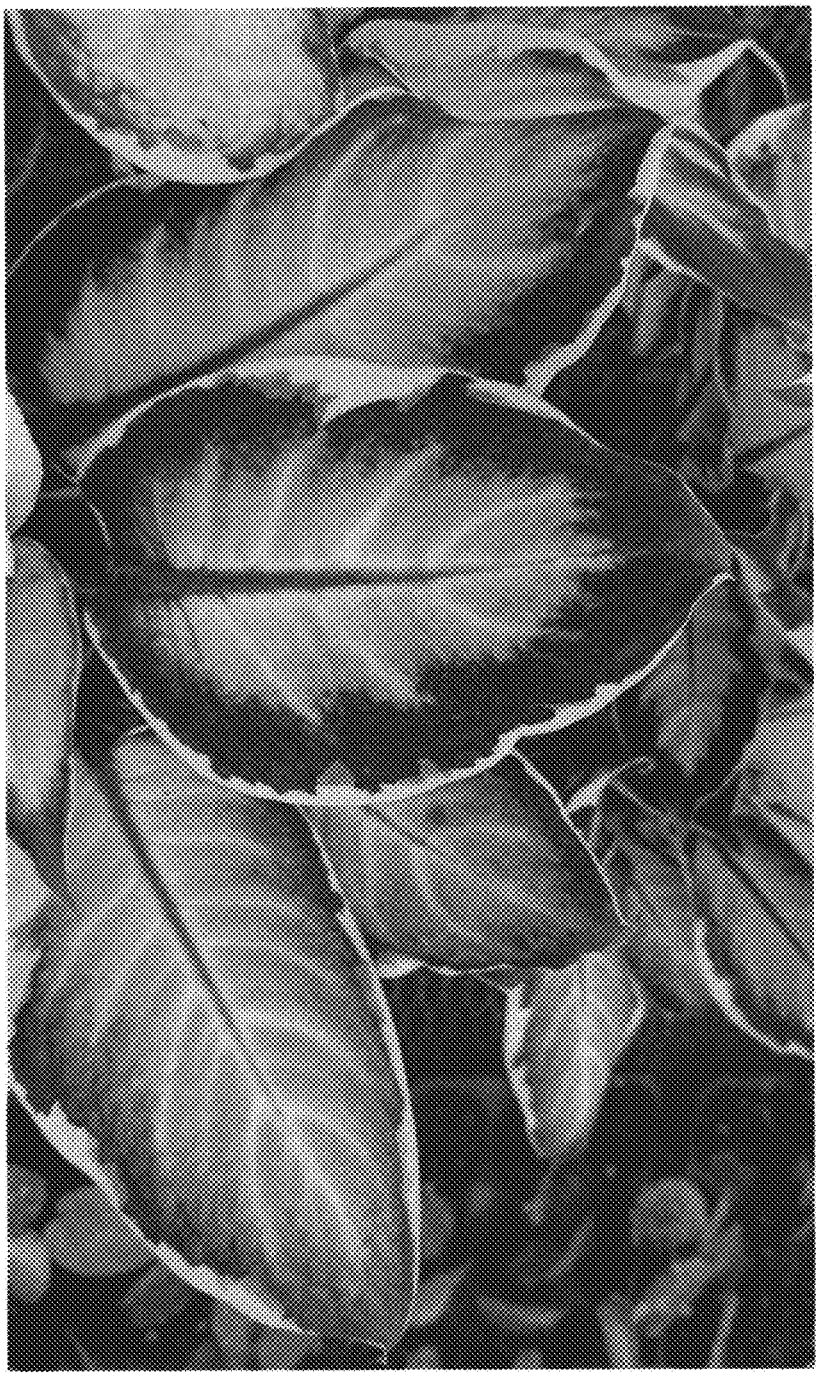
FIG. 2 illustrates in full color a close-up view of foliage of 'Cool Beauty'. The photographs were taken using conventional techniques and although colors may appear different from actual colors due to light reflectance it is as accurate as possible by conventional photographic techniques.

In the following description, color references are made to The Royal Horticultural Society Colour Chart 2007 except where general terms of ordinary dictionary significance are used. The following observations and measurements describe 'COOL BEAUTY' plants grown in a climate controlled greenhouse in Fukuoka-City, Japan. Temperatures ranged from 20° C. to 25° C. at night to 25° C. to 32° C. during the day. Light intensity was between 2500 and 3500 foot-candles. No artificial light, photoperiodic treatments were given to the plants. Measurements and numerical values represent averages of typical plant types.

Botanical classification: *Dieffenbachia sanguine* schott 'COOL BEAUTY'.

PROPAGATION

Time to initiate roots: About 14 days at approximately 25° C.

Time to produce a rooted plantlet: Approximately 8 to 12 weeks at approximately 22° to 25° C.

Root description: Fleshy, moderately thick, roots covered in fine lateral roots. Colored near RHS White 155A.

PLANT

Age of the plant described: Approximately 12 months from a single rooted tissue culture plantlet. Grown in a 16 cm pot.

Growth habit: Semi-horizontal, outwardly spreading, tender tropical.

Height: Approximately 35 cm.

Plant spread: Approximately 35 cm.

Growth rate: Moderate. Approximately 5-7 cm per month from rooted phase.

Branching characteristics: Branches emerging basally.

Diameter of stem: Approximately 2 cm near root. 1 cm on top.

Texture of stem: Smooth.

Color of stem: Near RHS Green 139C.

Stem strength: Strong.

Number of leaves per stem: Each branch has 5-7 leaves. 10 leaves on main stem.

FOLIAGE

Arrangement: Alternate.

*Average length.*—Approximately 15 cm.

*Average width.*—Approximately 7.5 cm at widest point.

*Shape of blade.*—Elliptic to ovate.

*Apex.*—Caudate.

*Base.*—Sheathing.

*Margin.*—Entire, very slightly undulating.

*Aspect.*—Slightly recurved downward, slightly undulate.

*Texture of top surface.*—Glabrous.

*Texture of bottom surface.*—Glabrous.

*Appearance of top surface.*—Matte.

*Appearance of lower surface.*—Matte.

*Color.*—Young foliage upper side: White margin near White 155D, interior halo near Green 136A, innermost section near Yellow-Green 145A and Green-White 157D. Young foliage under side: White margin near White 155D, interior halo near Green 136C, innermost section near Yellow-Green 145C and Green-White 157D. Mature foliage upper side: White margin near White 155D, interior halo near Green 134A, innermost section near Yellow-Green 145B and Green-White 157C. Mature foliage under side: White margin near White 155D, interior halo near Green 136C, innermost section near Yellow-Green 145C and Green-White 157C.

*Venation.*—Type: Pinnate Midrib characteristics: Protruding very slightly on upperside, significantly on underside. Venation coloration: upperside: Near RHS Green 138A. underside: Near RHS Green 137B.

Petiole

*Length.*—Average range for mature leaf 3 to 7 cm.

*Width.*—Average 1.0 cm.

*Color.*—Upperside: Near RHS Green 138B. Edge colored near Green-White 157D. Underside: Near RHS Green 138B. Edge colored near Green-White 157D.

*Angle.*—Upright, approximately 15° to center.

*Strength.*—Strong, moderately flexible.

*Texture.*—Smooth.

FLOWER

Flowering has not been observed.

OTHER CHARACTERISTICS

Disease/pest resistance: Neither resistance nor susceptibility to pathogens and pests common to *Dieffenbachia* have been observed.

Temperature tolerance: The new variety tolerates temperatures between 2 to 40° C.

Fruit/seed production: Not observed.

What is claimed is:

1. A new and distinct cultivar of *Dieffenbachia* plant named 'COOL BEAUTY' as herein illustrated and described.

* * * * *